US012090299B2

(12) United States Patent
Kim et al.

(10) Patent No.: US 12,090,299 B2
(45) Date of Patent: Sep. 17, 2024

(54) ELECTROOSMOTIC PUMP

(71) Applicant: EOFLOW CO., LTD., Seongnam-si (KR)

(72) Inventors: Jesse Jae Jin Kim, Seongnam-si (KR); Yong Chul Song, Seongnam-si (KR); Seung Ha Kim, Goyang-si (KR); Dae Jong Park, Seoul (KR)

(73) Assignee: EOFlow Co., Ltd., Seongnam-si (KR)

( * ) Notice: Subject to any disclaimer, the term of this patent is extended or adjusted under 35 U.S.C. 154(b) by 746 days.

(21) Appl. No.: 17/269,711

(22) PCT Filed: Aug. 20, 2019

(86) PCT No.: PCT/KR2019/010558
§ 371 (c)(1),
(2) Date: Feb. 19, 2021

(87) PCT Pub. No.: WO2020/040519
PCT Pub. Date: Feb. 27, 2020

(65) Prior Publication Data
US 2021/0196884 A1   Jul. 1, 2021

(30) Foreign Application Priority Data

Aug. 20, 2018 (KR) .................. 10-2018-0096819
Aug. 20, 2019 (KR) .................. 10-2019-0101608

(51) Int. Cl.
*A61M 5/142* (2006.01)
(52) U.S. Cl.
CPC .... *A61M 5/14216* (2013.01); *A61M 5/14224* (2013.01)

(58) Field of Classification Search
CPC . A61M 5/14216; A61M 5/14224; F04B 9/08; F04B 19/00; F04B 43/02; F04B 17/03; F04B 19/006
See application file for complete search history.

(56) References Cited

U.S. PATENT DOCUMENTS

| | | | |
|---|---|---|---|
| 6,277,257 B1 | 8/2001 | Paul et al. | |
| 2008/0029393 A1 | 2/2008 | Krumme | |
| 2008/0152522 A1 | 6/2008 | Pearson | |
| 2008/0260542 A1* | 10/2008 | Nishikawa | B01L 9/527 |
| | | | 417/48 |

(Continued)

FOREIGN PATENT DOCUMENTS

| | | | |
|---|---|---|---|
| JP | 2007-504402 A | 3/2007 | |
| KR | 10-2011-0048162 A | 5/2011 | |

(Continued)

OTHER PUBLICATIONS

International Search Report and Written Opinion mailed Nov. 26, 2019 in International Application No. PCT/KR2019/010558 in 8 pages. (including English translation of the ISR).

(Continued)

*Primary Examiner* — James D Ponton
(74) *Attorney, Agent, or Firm* — Knobbe, Martens, Olson & Bear, LLP

(57) ABSTRACT

Provided is an electroosmotic pump including a housing including a shaft hole, a membrane disposed between a first space arranged in a direction away from the shaft hole and a second space adjacent to the shaft hole, a first electrode body and a second electrode body arranged at opposite sides based on the membrane, a shaft extending to an outside of the housing through the shaft hole, and a first fluid included in an internal space of the housing.

8 Claims, 16 Drawing Sheets

(56) References Cited

U.S. PATENT DOCUMENTS

| | | | |
|---|---|---|---|
| 2011/0031268 A1 | 2/2011 | Anex et al. | |
| 2011/0203987 A1 | 8/2011 | Friedrichsen et al. | |
| 2012/0282111 A1* | 11/2012 | Nip | F04B 43/04 |
| | | | 417/48 |

FOREIGN PATENT DOCUMENTS

| | | |
|---|---|---|
| KR | 10-2017-0025062 A | 3/2017 |
| KR | 10-1752326 B1 | 6/2017 |
| KR | 10-2018-0024990 A | 3/2018 |
| KR | 10-1839806 B1 | 3/2018 |

OTHER PUBLICATIONS

Office Action of corresponding Chinese Patent Application No. 201980054301.3 issued on Mar. 22, 2022 in 12 pages.
Notice of Allowance of corresponding Chinese Patent Application No. 201980054301.3 issued on Mar. 31, 2023 in 4 pages.
Office Action of corresponding Japanese Patent Application No. 2021-509784 issued on Feb. 8, 2022 in 8 pages.
Notice of Allowance of corresponding Japanese Patent Application No. 2021-509784 issued on Sep. 6, 2022 in 5 pages.
Office Action of corresponding Korean Patent Application No. 10-2020-0037804 issued on Sep. 24, 2021 in 8 pages.
Notice of Allowance of corresponding Korean Patent Application No. 10-2020-0037804 issued on Mar. 2, 2022 in 7 pages.
Office Action of corresponding Korean Patent Application No. 10-2020-0140302 issued on Jul. 26, 2022 in 8 pages.
Notice of Allowance of corresponding Korean Patent Application No. 10-2020-0140302 issued on Oct. 14, 2022 in 10 pages.

* cited by examiner

ELECTROOSMOTIC PUMP

CROSS-REFERENCE TO RELATED APPLICATIONS

This application is the U.S. National Phase under 35. U.S.C. § 371 of International Application PCT/KR2019/010558, filed Aug. 20, 2019, which claims priority to Korean Patent Application No. 10-2018-006819, filed Aug. 20, 2018, and Korean Patent Application No. 10-2019-0101608, filed Aug. 20, 2019. The disclosure of each of the above-described applications is hereby incorporated by reference in its entirety.

BACKGROUND

Field

The present disclosure relates to an electroosmotic pump, and more particularly, to an electroosmotic pump using a fluid.

Description of the Related Art

Diabetes is a disease based on metabolic abnormalities that occur due to insufficient insulin which is one of the hormones secreted from the pancreas. A diabetic may use a method of injecting insulin into the body as one of active treatment methods. An insulin injection device may be used to inject insulin into the body to be suitable for a change in the blood sugar of the patient.

SUMMARY OF CERTAIN INVENTIVE ASPECTS

A mechanism for driving a drug injection device, e.g., an insulin injection device, may include driving members such as various kinds of motors or pumps. The present disclosure relates to a driving member and provides a pump capable of performing a fine pumping operation by using a fluid. However, the above technical features are exemplary, and the scope of the disclosure is not limited thereto.

According to an embodiment of the present disclosure, an electroosmotic pump includes: a housing including a shaft hole; a membrane disposed between a first space arranged in a direction away from the shaft hole and a second space adjacent to the shaft hole; a first electrode body and a second electrode body arranged at opposite sides based on the membrane; a shaft extending to an outside of the housing through the shaft hole; and a first fluid included in an internal space of the housing.

The shaft may reciprocate in a first direction from the first space to the second space and in a second direction opposite to the first direction.

According to the embodiment, a volume of the first fluid may be less than a volume of the internal space.

According to the embodiment, the first fluid may be in the first space and the second space, and a volume of the first fluid in the first space may be less than a volume of the first space.

According to the embodiment, the first space may include a first sub-space occupied by the first fluid and a second sub-space, and the reciprocation of the shaft may be changed according to a ratio of the volume of the second sub-space with respect to the first space.

According to the embodiment, the electroosmotic pump may further include a second fluid in the second sub-space.

The first fluid may be a liquid and the second fluid may be a gas.

According to another embodiment of the present disclosure, an electroosmotic pump includes: a housing including a shaft hole in a side thereof; a shaft extending to an outside of the housing through the shaft hole; a membrane arranged in an internal space that is defined by an inner surface of the housing and the shaft; a first electrode body arranged at a first side of the membrane; a second electrode body arranged at a second side of the membrane, wherein the second side is opposite to the first side; and a fluid included in the internal space.

According to the embodiment, the internal space may include a first space and a second space at opposite sides of the membrane, the fluid may include a first fluid in the first space, and a volume of the first fluid in the first space may be less than a volume of the first space.

According to another embodiment of the present disclosure, an electroosmotic pump includes: a housing including a shaft hole; a membrane arranged between a first space disposed in a direction away from the shaft hole and a second space adjacent to the shaft hole; a first electrode body and a second electrode body arranged at opposite sides of the membrane; a shaft extending to an outside of the housing through the shaft hole; a deformation portion communicating with a side of the housing, in which the first space is formed, including a third space connecting to the first space, and being deformable; and a first fluid included in an internal space of the housing.

According to the embodiment, the electroosmotic pump may further include a second fluid in the first space and the third space, wherein the first fluid may be a liquid and the second fluid may be a gas.

Other aspects, features and advantages of the disclosure will become better understood through the accompanying drawings, the claims and the detailed description.

According to one or more embodiments, a reciprocating movement of a shaft may be finely controlled by using a pressure of a fluid.

Also, forward or backward movement of a shaft may be accurately controlled due to an elastic deformation of a deformation portion.

However, the above effects are exemplary and the scope of the present disclosure is not limited thereto.

DETAILED DESCRIPTION OF CERTAIN ILLUSTRATIVE EMBODIMENTS

Figure 1:
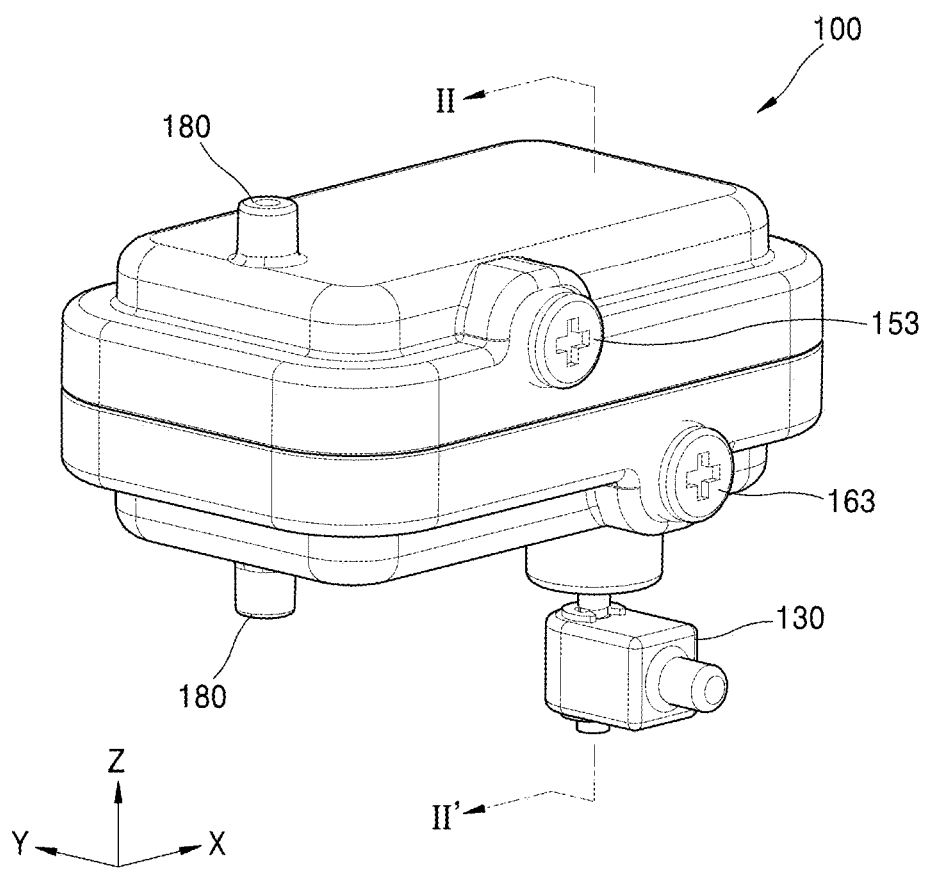
FIG. 1 is a perspective view of a pump according to an embodiment of the present disclosure.

As the present disclosure allows for various changes and numerous embodiments, particular embodiments will be illustrated in the drawings and described in detail in the written description. The attached drawings for illustrating one or more embodiments are referred to in order to gain a sufficient understanding, the merits thereof, and the objectives accomplished by the implementation. However, the embodiments may have different forms and should not be construed as being limited to the descriptions set forth herein.

The embodiments will be described below in more detail with reference to the accompanying drawings. Those components that are the same or are in correspondence are rendered the same reference numeral regardless of the figure number, and redundant explanations are omitted.

While such terms as "first," "second," etc., may be used to describe various components, such components are not be limited to the above terms. The above terms are used only to distinguish one component from another.

An expression used in the singular encompasses the expression of the plural, unless it has a clearly different meaning in the context.

In the present specification, it is to be understood that the terms "including," "having," and "comprising" are intended to indicate the existence of the feature or components disclosed in the specification, and are not intended to preclude the possibility that one or more other features or components may exist or may be added.

Sizes of components in the drawings may be exaggerated for convenience of explanation. In other words, since sizes and thicknesses of components in the drawings are arbitrarily illustrated for convenience of explanation, the following embodiments are not limited thereto.

In the embodiments below, it will be understood when areas or elements are referred to as being "connected," they may be directly connected or an intervening portion may be present between areas or elements.

Figure 2:
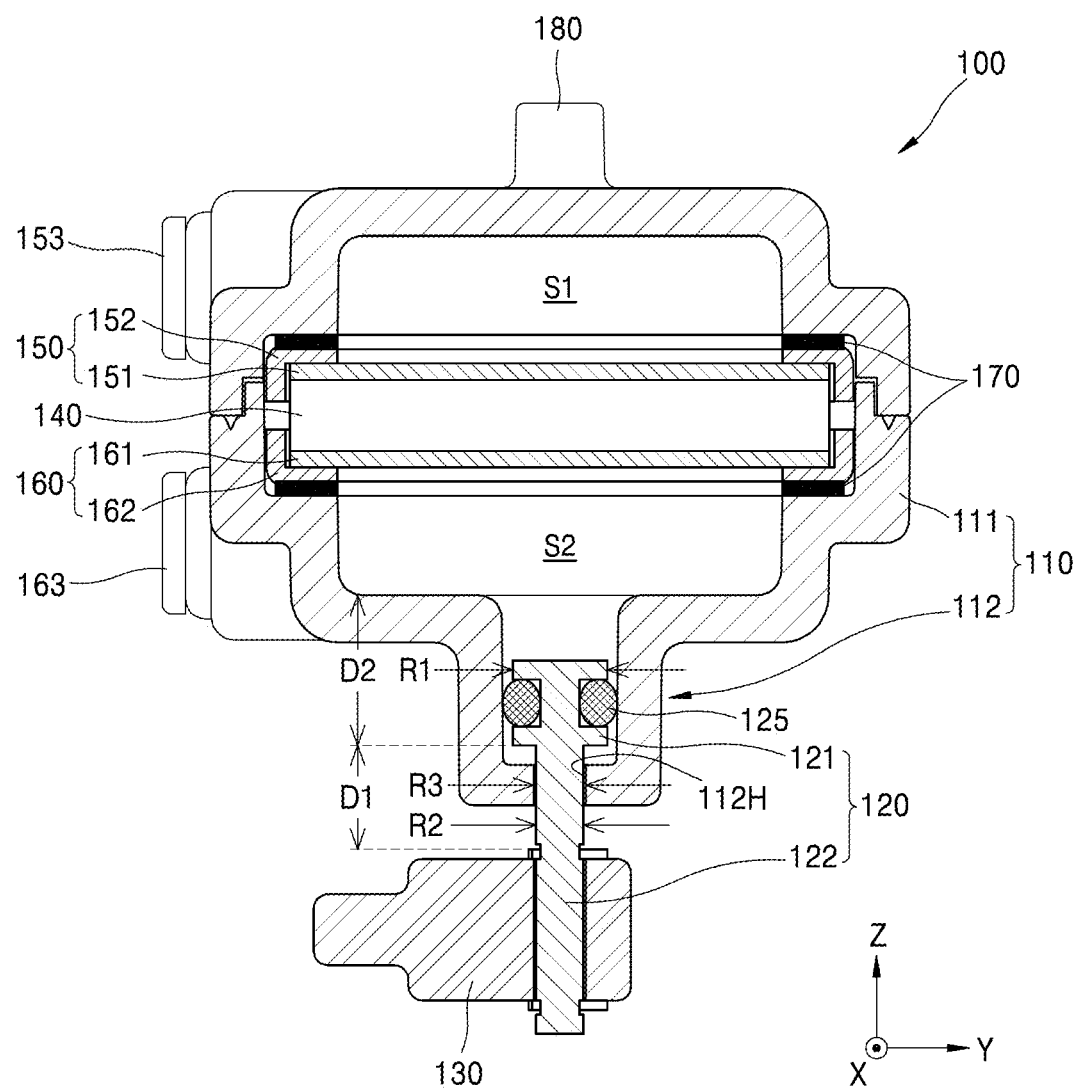
FIG. 2 is a cross-sectional view of the electroosmotic pump taken along line II-II' of FIG. 1.

FIG. 1 is a perspective view of an electroosmotic pump according to an embodiment of the present disclosure, and FIG. 2 is a cross-sectional view of the electroosmotic pump taken along line II-II' of FIG. 1.

Referring to FIGS. 1 and 2, a housing 110 of an electroosmotic pump (hereinafter, referred to as 'pump') 100 includes a shaft hole 112H in a side thereof, and a shaft 120 having a certain length may extend to outside of the housing 110 through the shaft hole 112H. In an embodiment, the shaft hole 112H may be formed in a protrusion 112 that extends to a side with respect to a main body 111 of the housing 110, and a diameter of the protrusion 112 may be less than that of the main body 111.

A first portion 121 of the shaft 120 is in the housing 110, and a second portion 122 of the shaft 120 extends to the outside of the housing 110 after passing through the shaft hole 112H as described above. The shaft 120 may reciprocate in an up-and-down direction (Z-direction) in FIGS. 1 and 2. When the shaft 120 reciprocates, the first portion 121 may linearly reciprocate in an internal space of the housing 110, for example, an internal space corresponding to the protrusion 112. A diameter R1 of the first portion 121 of the shaft 120 is greater than a diameter R3 of the shaft hole 112H, the first portion 121 does not fall out of the housing 110.

The second portion 122 of the shaft 120 has a diameter R2 that is less than the diameter R3 of the shaft hole 112H, and in order to prevent the second portion 122 from falling out of the shaft hole 112H, the second portion 122 may be coupled to a movement controller 130 that is provided outside the housing 110.

A sealing material 125 may be disposed on a side surface of the first portion 121 of the shaft 120. The internal space of the housing 110, e.g., a space defined by an inner surface of the housing 110 and an inner surface of the shaft 120, is a sealed space, and there is a fluid in the internal space and the sealing material 125 may prevent leakage of the fluid through a gap between the housing 110 and the shaft 120. In FIG. 2, the fluid is omitted for convenience of description.

According to an embodiment, as shown in FIG. 2, the sealing material 125 may be an O-ring type that may cover the side surface of the first portion 121, and the leakage of the fluid in the housing 110 to the outside of the housing 110 through the shaft hole 112H may be prevented by the sealing material 125. The leakage of the fluid may be effectively prevented by forming a first distance D1 from the first portion 121 of the shaft 120 to the movement controller 130 to be equal to or less than an internal length D2 of the protrusion 112.

A membrane 140 may be disposed in the internal space of the housing 110, e.g., the internal space corresponding to the main body 111. The internal space includes a first space S1 and a second space S2 that are at opposite sides of the membrane 140. In FIG. 2, based on the membrane 140, a space farther from the shaft 120 is represented as the first space S1 and a space closer to the shaft 120 is represented as the second space S2.

The membrane 140 may have a porous structure through which the fluid and ions may pass. The membrane 140 may include, for example, a frit-type membrane that is fabricated by sintering spherical silica with heat. For example, the spherical silica used to form the membrane may have a diameter of about 20 nm to about 500 nm, for example, a diameter of about 30 nm to about 300 nm, and in particular, a diameter of about 40 nm to about 200 nm. When the diameter of the spherical silica satisfies the above range, a pressure caused by a first fluid passing through the membrane 140, that is, a sufficient pressure to move the shaft 120, may be generated.

In the above embodiment, the membrane 140 includes the spherical silica, but the membrane 140 is not limited thereto. In another embodiment, a kind of the material included in the membrane 40 is not particularly limited, provided that the material may cause an electrokinetic phenomenon due to zeta potential, for example, porous silica or porous alumina.

The membrane 140 may have a thickness of about 20 μm to about 10 mm, for example, about 300 μm to about 5 mm, and in particular, about 1000 μm to about 4 mm.

A first electrode body 150 and a second electrode body 160 are respectively arranged on opposite sides of the membrane 140. The first electrode body 150 may include a first porous plate 151 and a first electrode strip 152 arranged on a first side of the membrane 140. The second electrode body 160 may include a second porous plate 161 and a second electrode strip 162 arranged on a second side of the membrane 140.

The first and second porous plates 151 and 161 may be arranged to be respectively in contact with opposite main surfaces of the membrane 140. The first and second porous plates 151 and 161 may effectively move the fluid and ions through the porous structures. The first and second porous plates 151 and 161 may each have a structure in which an electrochemical reaction material is formed on a porous base layer. The electrochemical reaction material may be electrodeposited or coated on the porous base layer by a method, for example, electroless plating, vacuum deposition, coating, sol-gel processing, etc.

The porous base layer may include an insulator. For example, the porous base layer may include one or more selected from a non-conductive ceramic material, a non-conductive polymer resin, a non-conductive glass material, and a combination thereof.

The non-conductive ceramic material may include, but is not limited to, one or more selected from the group consisting of rock wool, gypsum, ceramics, cement, and a combination thereof, and in particular, one or more selected from the group consisting of rock wool, gypsum, and a combination thereof.

The non-conductive polymer resin may include, but is not limited to, one or more selected from the group consisting of: for example, synthetic fiber selected from the group consisting of polypropylene, polyethylene terephthalate, polyacrylonitrile, and a combination thereof; natural fiber selected from the group consisting of wool, cotton, and a combination thereof; a sponge; an organism, e.g., a porous material derived from a bone of an organism; and a combination thereof.

The non-conductive glass may include, but is not limited to, one or more selected from the group consisting of glass wool, glass frit, porous glass, and a combination thereof.

The porous base layer may have a pore size of about 0.1 μm to about 500 for example, about 5 μm to about 300 μm, and in particular, about 10 μm to about 200 μm. When the pore size of the porous support satisfies the above range, the fluid and ions may be effectively moved, to thereby improve stability, lifespan property, and efficiency of the pump 100.

The electrochemical reaction material may include a material that may generate a pair of reactions in which an oxidizing electrode and a reducing electrode exchange positive ions, e.g., hydrogen ions, during electrode reactions of the first and second electrode bodies 150 and 160, and at the same time, may constitute a reversible electrochemical reaction. The electrochemical reaction material may include one or more selected from the group consisting of, for example, silver/silver oxide, silver/silver chloride, MnO (OH), polyaniline, polypyrrole, polythiophene, polythionine, quinone-based polymer, and a combination thereof.

The first and second strips 152 and 162 may be arranged at edges of the first and second porous plates 151 and 161, and may be connected to first and second terminals 153 and 163 on the outside of the housing 110. The first and second strips 152 and 162 may include a conductive material such as silver, copper, etc.

The fluid included in the internal space of the housing 110 may include a first fluid and a second fluid having different phases from each other. The first fluid may include a liquid such as water, and the second fluid may include a gas such as air. The first fluid in the internal space does not entirely fill the internal space. That is, a volume of the internal space is greater than a volume of the first fluid in the internal space. In the internal space, the second fluid exists in the region where there is no water.

Sealing materials 170 are arranged at opposite sides of a structure including the membrane 140, the first electrode body 150, and the second electrode body 160. Each of the sealing materials 170 may have a loop shape having an area corresponding to the edge of the structure. The fluid, e.g., the first fluid, moves from the first space S1 to the second space S2 or in the reverse direction along a thickness direction of the membrane 140 so as to pass through the membrane 140, and the sealing material 170 blocks a gap between the inner surface of the housing 110 and the above structure to prevent the liquid from moving to the gap.

The fluid may enter the internal space through an injection port 180 as shown in FIG. 1. In an embodiment, the first fluid is entirely filled in the internal space through injection ports 180 at opposite sides, and then, the first fluid is partially discharged through one injection port 180 and the injection ports 180 are closed. Thus, the first fluid and the second fluid may exist in the internal space of the housing 110.

Hereinafter, the behavior of the fluid and movement of the shaft according to the behavior will be described with reference to FIGS. 3A to 5.

Figure 3A:
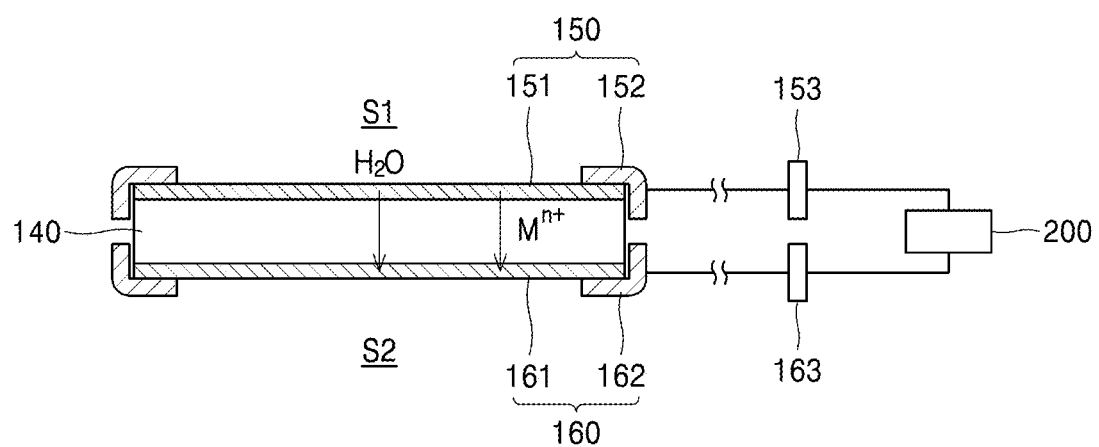
FIGS. 3A and 3B are schematic diagrams showing reactions of first and second electrode bodies around a membrane, according to an embodiment of the present disclosure.
Figure 3B:
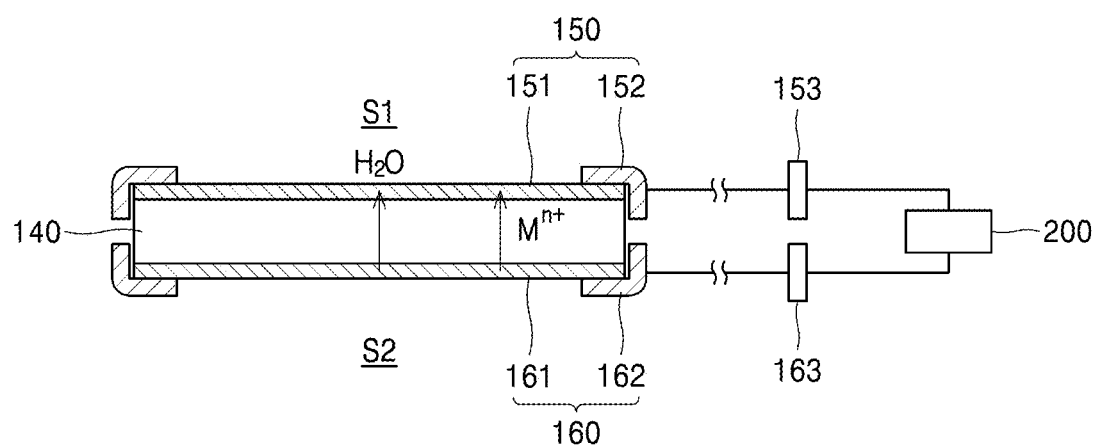

FIGS. 3A and 3B are schematic diagrams showing reactions of first and second electrode bodies around a membrane.

Referring to FIGS. 3A and 3B, the first electrode body 150 and the second electrode body 160 are electrically connected to a power supply unit 200 via the first and second terminals 153 and 163, respectively. By supplying a voltage supplied by the power supply unit 200 after alternately changing the polarity of the voltage, a moving direction of the liquid such as water may be changed.

In an embodiment, an example in which the silver/silver oxide is used as the electrochemical reaction material and the first fluid is a solution including water will be described.

As shown in FIG. 3A, when the first electrode body 150 is an oxidizing electrode and the second electrode body 160 is a reducing electrode, a reaction of $Ag(s)+H_2O \rightarrow Ag_2O(s)+2H^++2e^-$ occurs in the first electrode body 150 and a reaction of $Ag_2O(s)+2H^++2e^- \rightarrow Ag(s)+H_2O$ occurs in the second electrode body 160.

Cations ($M^{n+}$, e.g., hydrogen ions) generated according to the oxidation reaction in the first electrode body 150 move toward the second electrode body 160 through the membrane 140 due to a voltage difference, and at this time, water ($H_2O$) moves together with the cations and a certain pressure may be generated.

After that, as shown in FIG. 3B, when the polarity of the voltage supplied by the power supply unit 200 is reversed, the electrochemical reaction material that has been consumed when the first electrode body 150 is previously used as the oxidizing electrode is recovered when the first electrode body 150 is used as the reducing electrode. Likewise, the electrochemical reaction material may be also recovered in the reducing electrode, and thus, the first and second electrode bodies 150 and 160 may continuously react accordingly to the voltage supply from the power supply unit 200. Unlike in FIG. 3A, when the polarity of the voltage supplied to the first and second electrode bodies 150 and 160, as shown in FIG. 3B, the cations ($M^{n+}$, e.g., hydrogen ions) and the water ($H_2O$) move from the second space S2 to the first space S1.

Figure 4A:
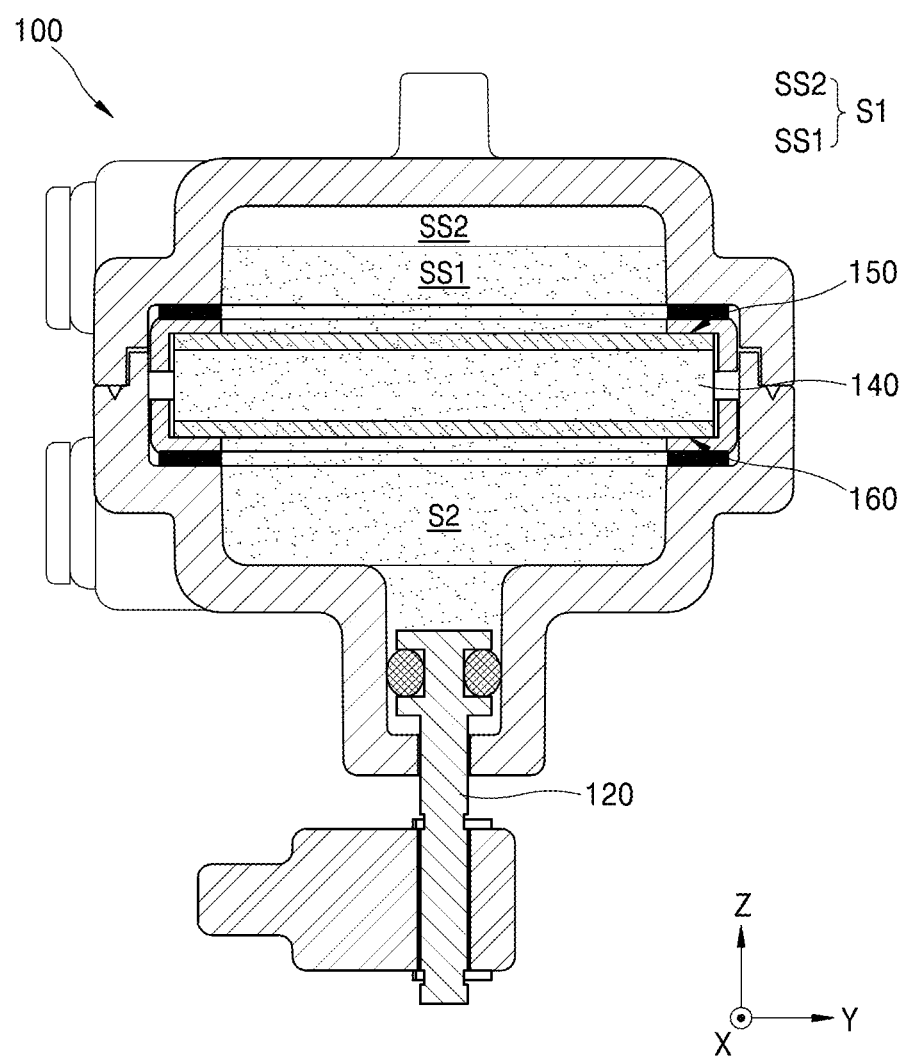
FIGS. 4A and 4B are cross-sectional views for describing a reciprocation movement of a shaft according to an embodiment of the present disclosure.
Figure 4B:
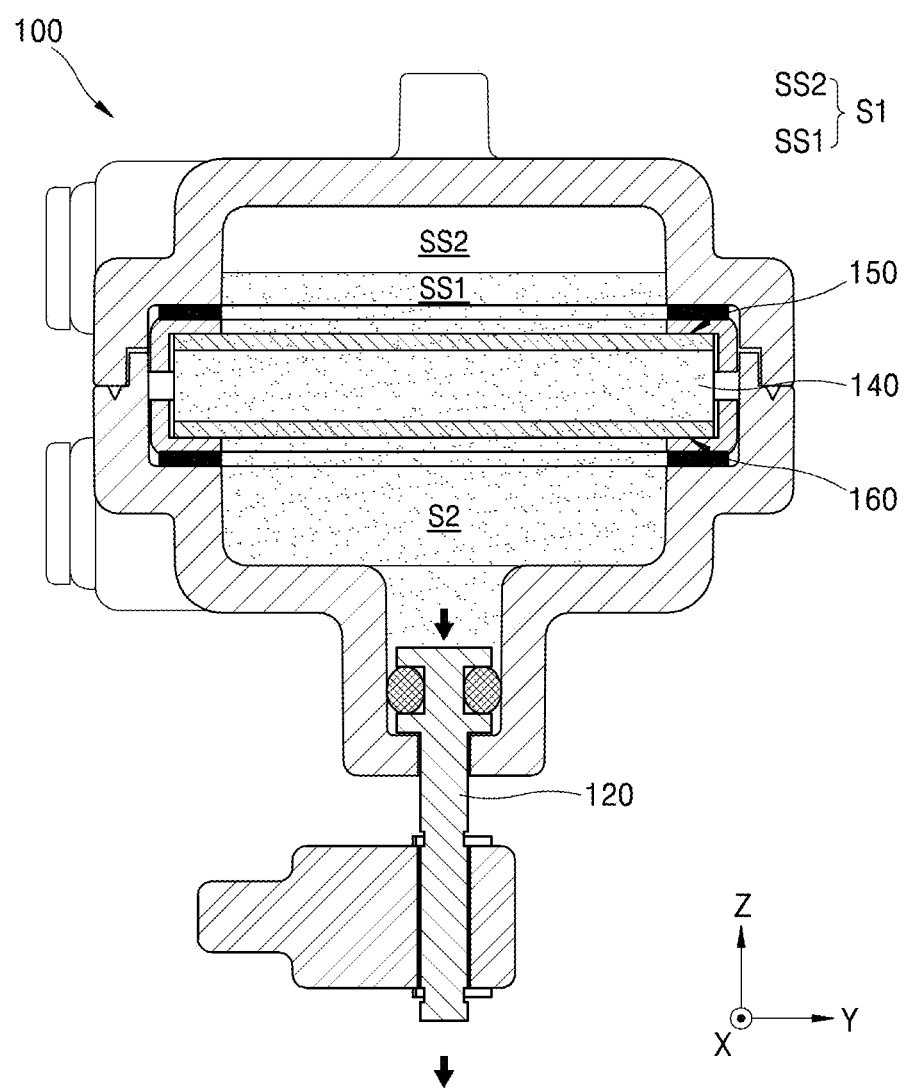

FIGS. 4A and 4B are cross-sectional views for describing a reciprocating movement of the shaft. FIG. 4A shows a state before the shaft moves and FIG. 4B shows a state after the shaft moves. FIG. 4A may be understood as a state before the voltage is applied to the first and second electrode bodies 150 and 160 by the power supply unit 200 as described above with reference to FIG. 3A.

Referring to FIG. 4A, the first fluid that is the liquid such as water exists in the internal space of the housing 110, and the volume of the first fluid in the internal space is less than the volume of the internal space. The second fluid including a gas such as the air exists in the region of the internal space, in which the liquid does not exist.

For example, the first fluid exists in each of the first and second spaces S1 and S2, and the first fluid and the second fluid coexist in the first space S1, while the volume of the first fluid in the first space S1 may be less than a volume of the first space S1. The first fluid also exists in the second space S2, but the second fluid does not exist in the second space S2, unlike in the first space S1. Hereinafter, for convenience of description, in the first space S1, a space in which the first fluid, that is, the liquid, exists is referred to as a first sub-space SS1 and a space in which the second fluid, that is, the gas, exists is referred to as a second sub-space SS2. The first sub-space SS1 and the second sub-space SS2 may constitute the first space S1. For example, in the first space S1, a remaining space except for the first sub-space SS1 may be the second sub-space SS2.

In the state of FIG. 4A, when the power supply unit 200 supplies the voltage to the first and second electrode bodies 150 and 160 as described above with reference to FIG. 3A, the reaction described above with reference to FIG. 3A occurs and the cations (e.g., hydrogen ions) move in a first direction (−Z direction in FIG. 4) from the first space S1 to the second space S2. Here, the first fluid (e.g., H$_2$O) in the first space S1 is moved with the cations in the first direction through the membrane 140, and then, a pressure is generated. In addition, the shaft 120 linearly moves in the first direction due to the pressure as shown in FIG. 4B. When the first fluid (e.g., H$_2$O) in the first space S1 moves to the second space S2, a ratio of the volume of the first sub-space SS1 with respect to the volume of the first space S1 is reduced, whereas a ratio occupied by the second sub-space SS2 in the first space S1 increases.

On the contrary, when the power supply unit 200 changes the polarity of the voltage and supplies the voltage to the first and second electrode bodies 150 and 160 in the state of FIG. 4B as described above with reference to FIG. 3B, the cations (e.g., hydrogen ions) and the first fluid (e.g., water) move in a second direction (Z-direction of FIG. 4) from the second space S2 to the first space S1, and the shaft 120 is moved to the original position as shown in FIG. 4A.

When the power supply unit 200 alternately changes the polarity of the voltage supplied to the first and second electrode bodies 150 and 160, the shaft 120 moves in the first direction and then moves in the reverse direction, that is, in the second direction, and then, moves back in the first direction, that is, may reciprocate.

The reciprocating movement of the shaft 120 may be described as a change according to a ratio of the volume of the space in which the second fluid exists, that is, the volume of the second sub-space SS2, with respect to the first space S1.

Figure 5:
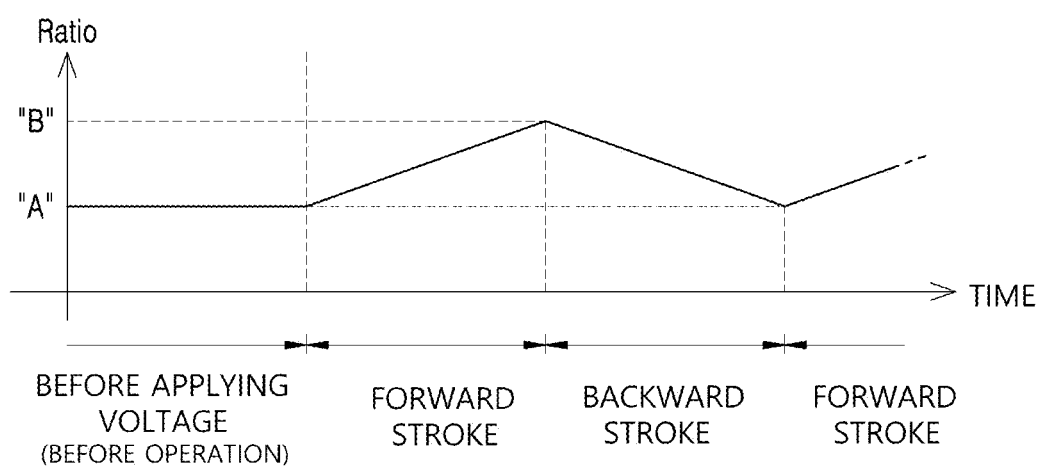
FIG. 5 is a graph showing a ratio of a volume (VSS2) of a second sub-space with respect to a volume (VS1) of a first space according to a reciprocating movement of a shaft.

FIG. 5 is a graph showing a ratio of a volume (VSS2) of the second sub-space with respect to a volume (VS1) of the first space according to the reciprocating movement of the shaft.

When a ratio of the volume of the second sub-space SS2 with respect to the volume of the first space S1 (ratio=VSS2/VS1) in a state before the power supply unit 200 applies the voltage to the first and second electrode bodies 150 and 160, that is, a state before driving the pump 100, is referred to as "A", the ratio increases to "B" during a forward stroke of the shaft 120, that is, when the shaft 120 moves in the first direction (A<B, A is greater than 0 and B is less than 1).

In a backward stroke, in the second direction, of the shaft 120 that has proceeded, the above ratio decreases from B to A, but the ratio is not less than A. When the ratio is less than A during the backward stroke, the shaft 120 enters the inside of the housing 110 further, or the encapsulation of the internal space of the housing 110 that is the sealed space is released, and thus, leakage of the fluid, etc. may occur.

The pump 100 described above with reference to FIGS. 4A and 4B may be fabricated by assembling elements (main body, sealing material, etc.) in a state in which the shaft 120 is relatively retracted. In another embodiment, the pump 100 may be fabricated by assembling the elements (main body, sealing material, etc.) in a state in which the shaft 120 is relatively moved forward.

When the shaft 120 moves forward or backward, the second fluid (e.g., air) in the second sub-space SS2 may be slightly compressed or slightly expanded. A certain force may be stored in the second fluid according to the compression or expansion of the second fluid, and the force may be applied to the piston 120. An accurate control on the forward and backward strokes of the piston 120 may affect an injection dose of a drug in a drug injection device in which the pump 100 is used. Therefore, the forward and backward strokes of the piston 120 may be designed taking the above-described force into account. Alternatively, in order to accurately control the forward and backward strokes of the piston 120, the force stored in the second fluid may be removed. For example, as shown in FIG. 6, a hole 111H may be formed in the main body 111 and the outside and the inside of the pump 100 may be separated by a breathable film 190.

Figure 6:
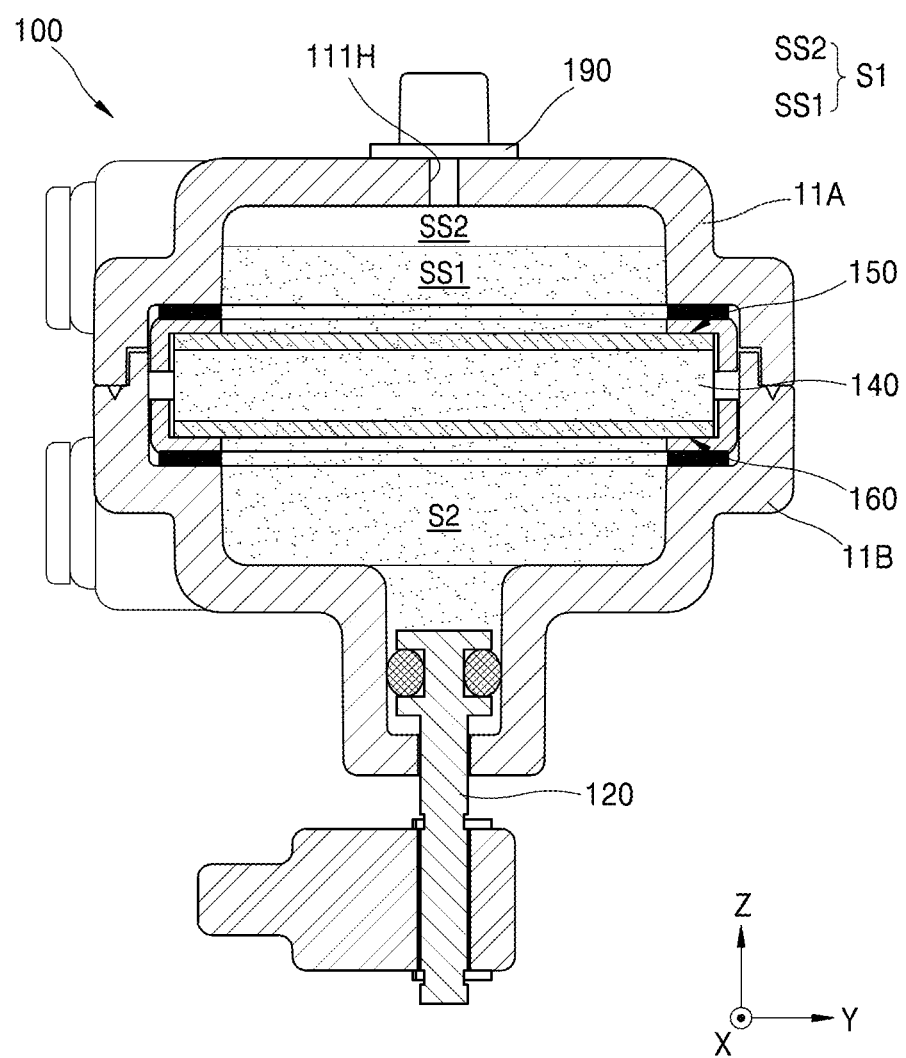
FIG. 6 is a cross-sectional view of a pump according to another embodiment of the present disclosure.

FIG. 6 is a cross-sectional view of a pump according to another embodiment of the present disclosure. The pump shown in FIG. 6 may have a similar structure to that of the pump described above with reference to FIGS. 1 to 5, but may further include the breathable film 190.

The main body 111 may include a first sub-main body 111A and a second sub-main body 111B. The first sub-main body 111A and the second sub-main body 111B are coupled to each other with the membranes 140 therebetween, and this structure may be also applied to the embodiment described above with reference to FIGS. 1 to 4B.

The main body 111 may include the hole 111H. The hole 111H is located opposite to the second sub-main body 111B that accommodates the shaft 120, with the membrane 140 in the center therebetween. For example, the hole 111H may be formed in the first sub-main body 111A.

The hole 111H may be covered by the breathable film 190. Therefore, the second sub-space SS2 may not be spatially connected to the outer space due to the breathable film 190. The breathable film 190 may be formed at a location corresponding to the center of the first space S1. In FIG. 6, a pair of the hole 111H and the breathable film 190 are provided, but in another embodiment, plural pairs of the holes 111H and corresponding breathable films 190 may be provided. Alternatively, one breathable film 190 may be provided with respect to a plurality of holes 111H, and in this case, the breathable film 190 may have an area that is enough to entirely cover a surface (upper surface in FIG. 6) of the first sub-main body 111A.

The breathable film 190 is a film that blocks the liquid and transmits the gas, and thus the first fluid (e.g., water) of the pump 100 does not pass through the breathable film 190. For example, the breathable film 190 may include, for example, Tyvek® from Dupont, Inc. On the contrary, the second fluid in the pump 100 or the external air may pass through the breathable film 190, and in this case, the force generated when the piston 120 moves forward and backward may be prevented from being stored in the second fluid.

Hereinafter, a structure, operating principles, and effects of the pump 100 according to another embodiment will be described below.

Figure 7:
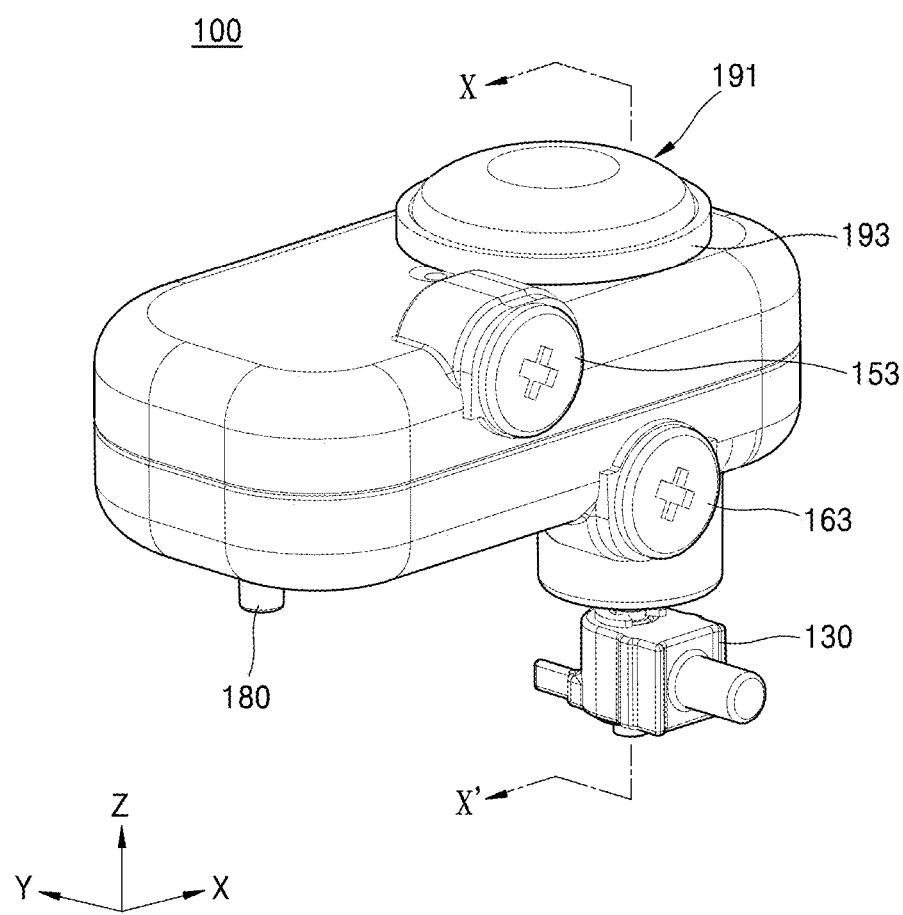
FIG. 7 is a perspective view of an electroosmotic pump according to another embodiment of the present disclosure.
Figure 8A:
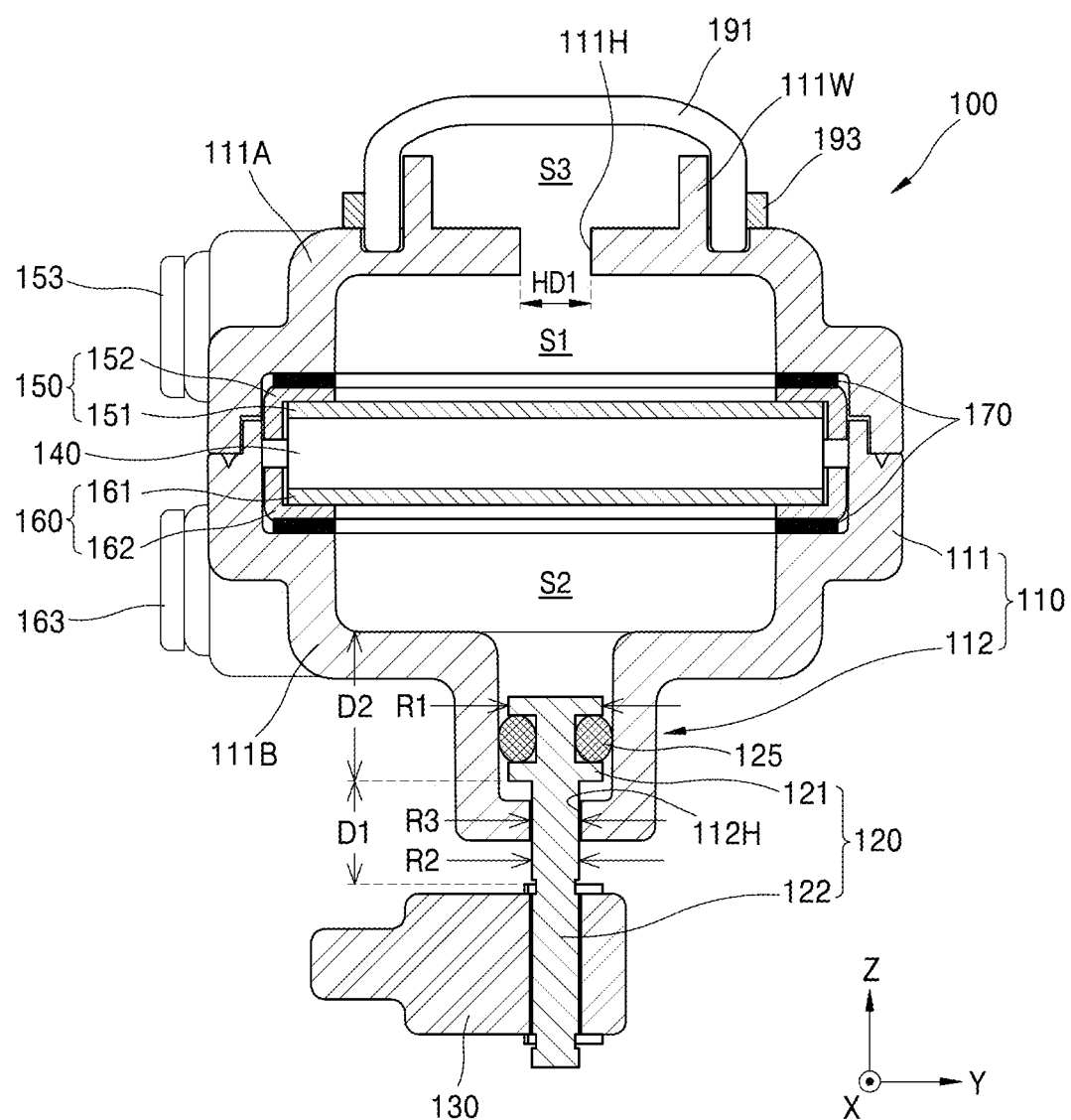
FIGS. 8A and 8B are cross-sectional views of the electroosmotic pump taken along line X-X' of FIG. 7.
Figure 8B:
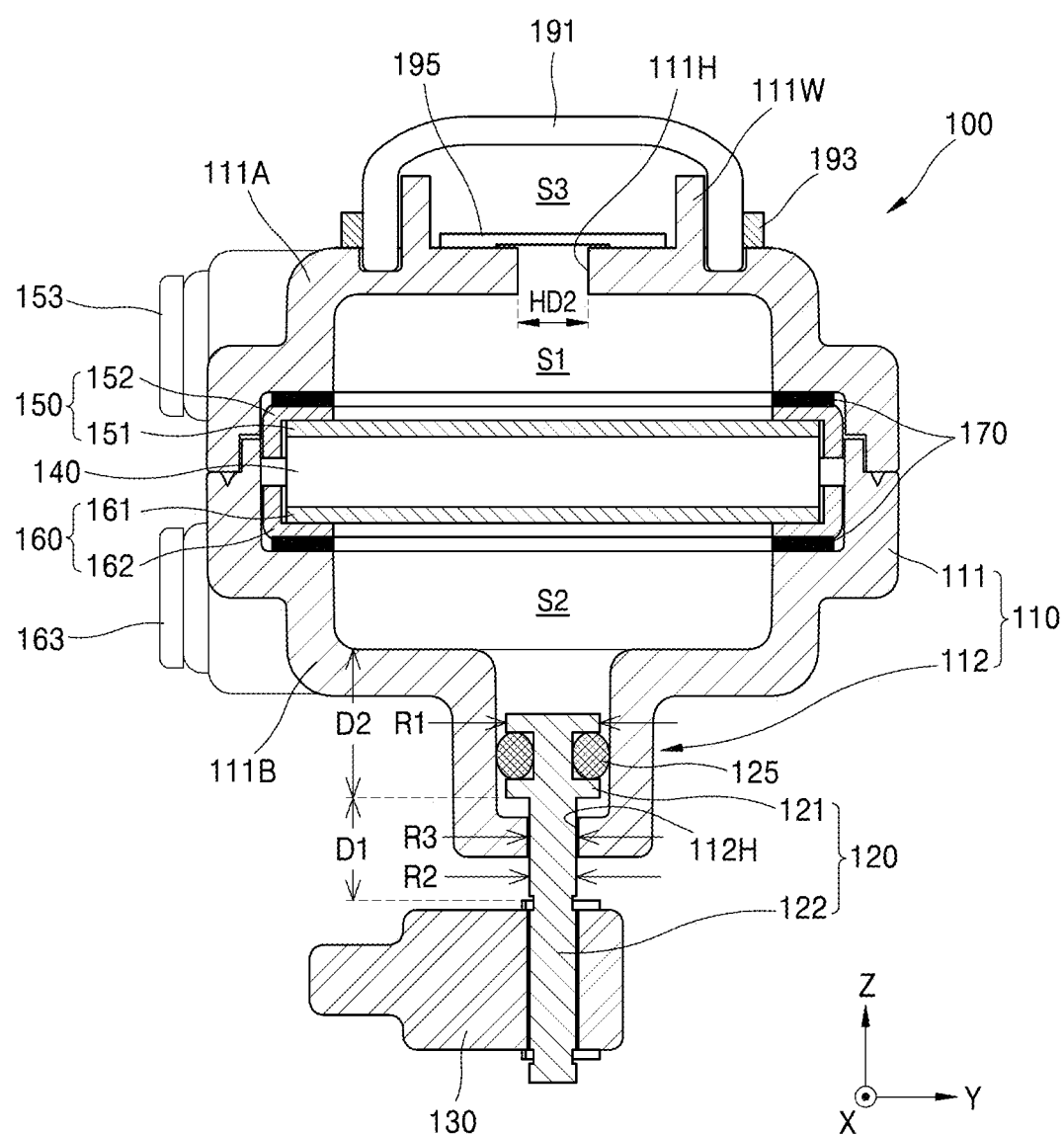
Figure 9A:
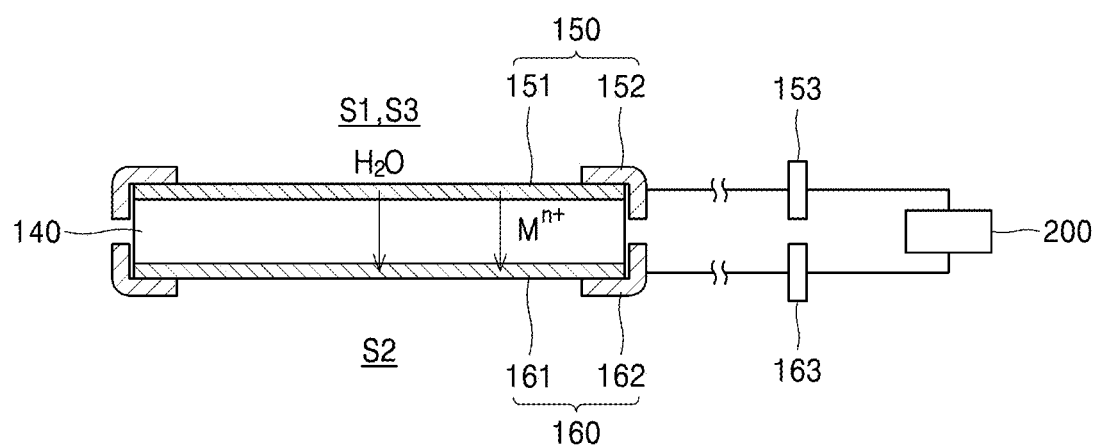
FIGS. 9A and 9B are schematic diagrams showing reactions of first and second electrode bodies based on a membrane, according to embodiments of the present disclosure.
Figure 9B:
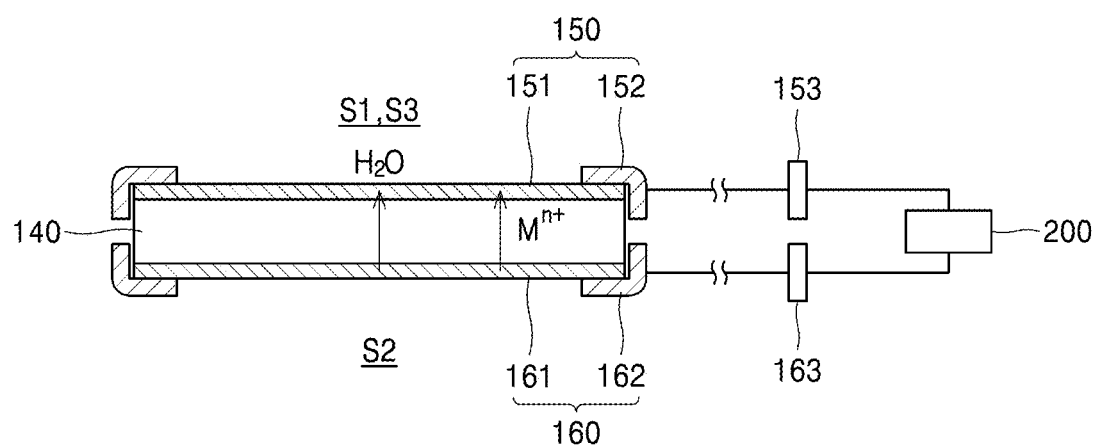
Figure 10A:
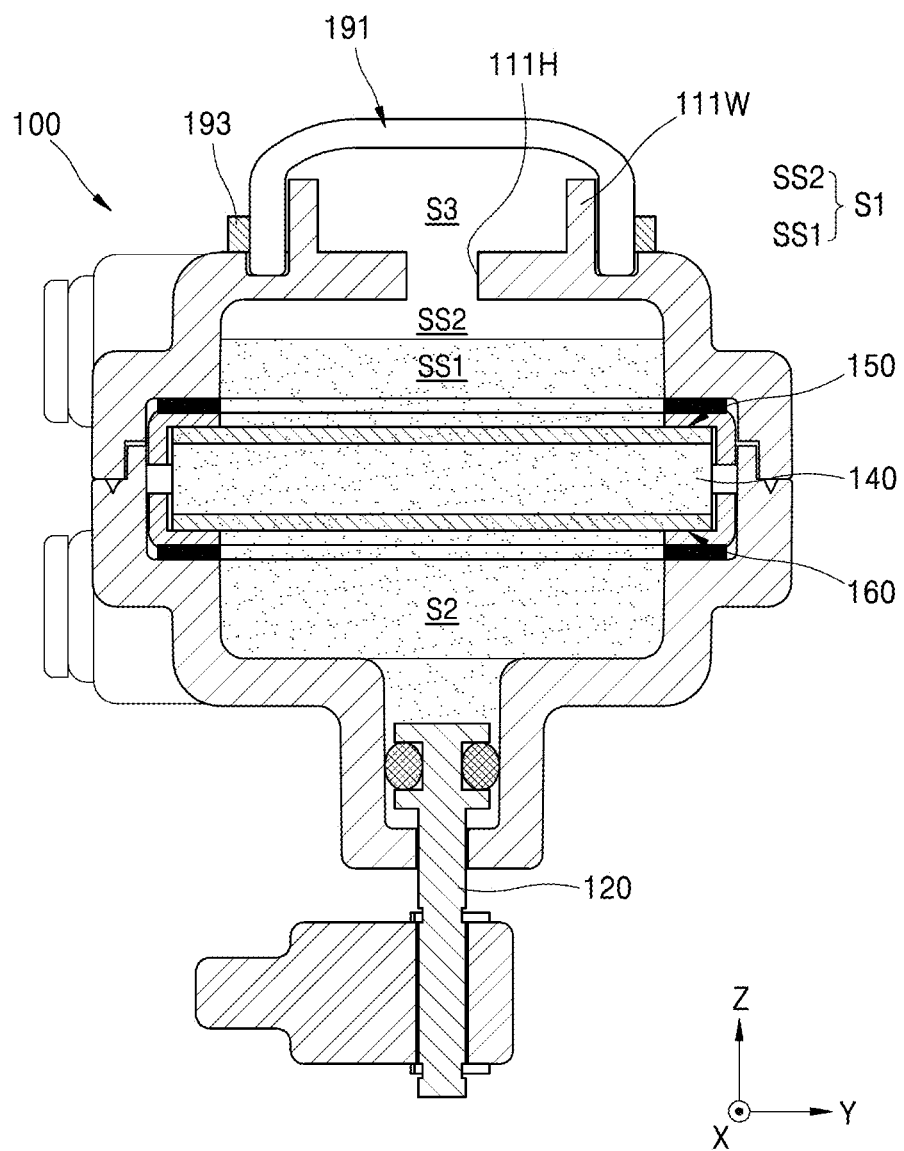
FIGS. 10A to 10C are cross-sectional views for describing a reciprocating movement of a shaft.
Figure 10B:
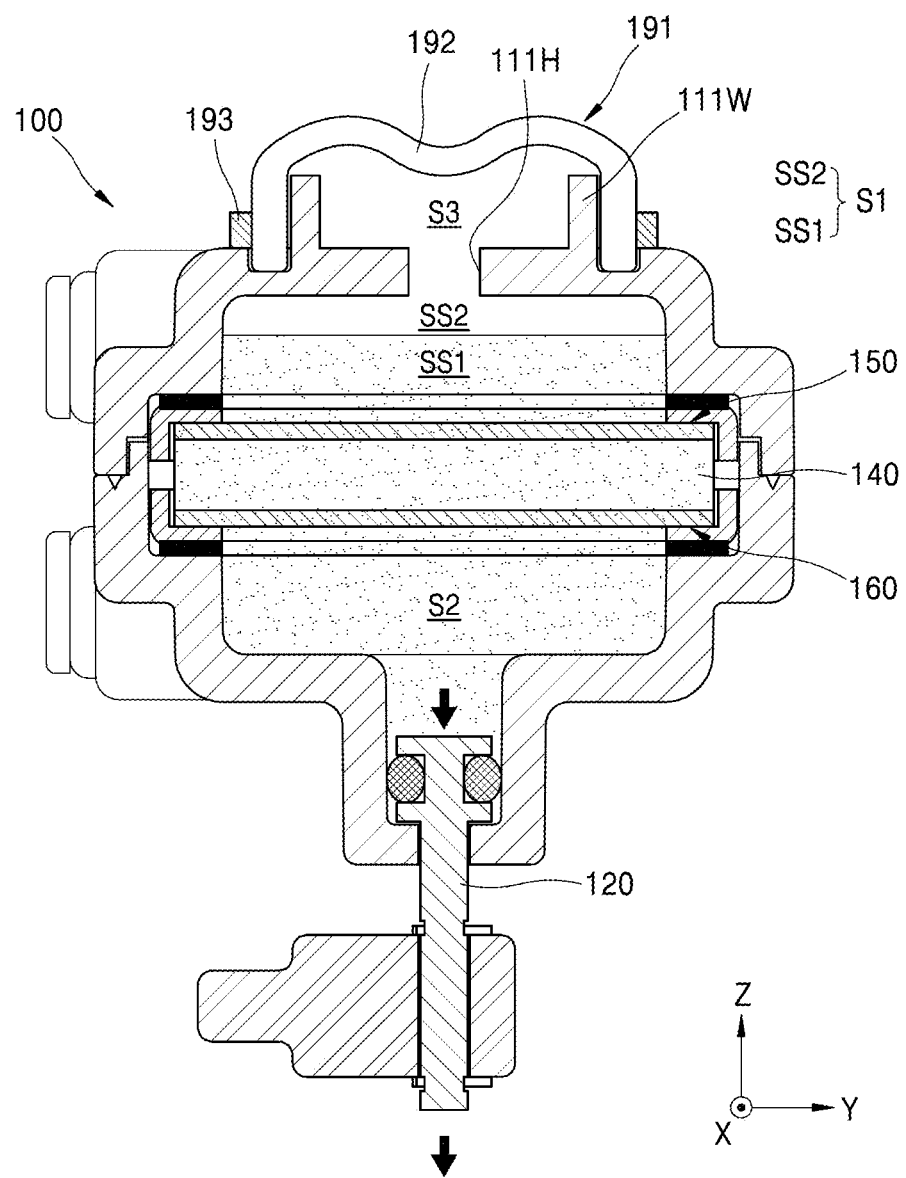
Figure 10C:
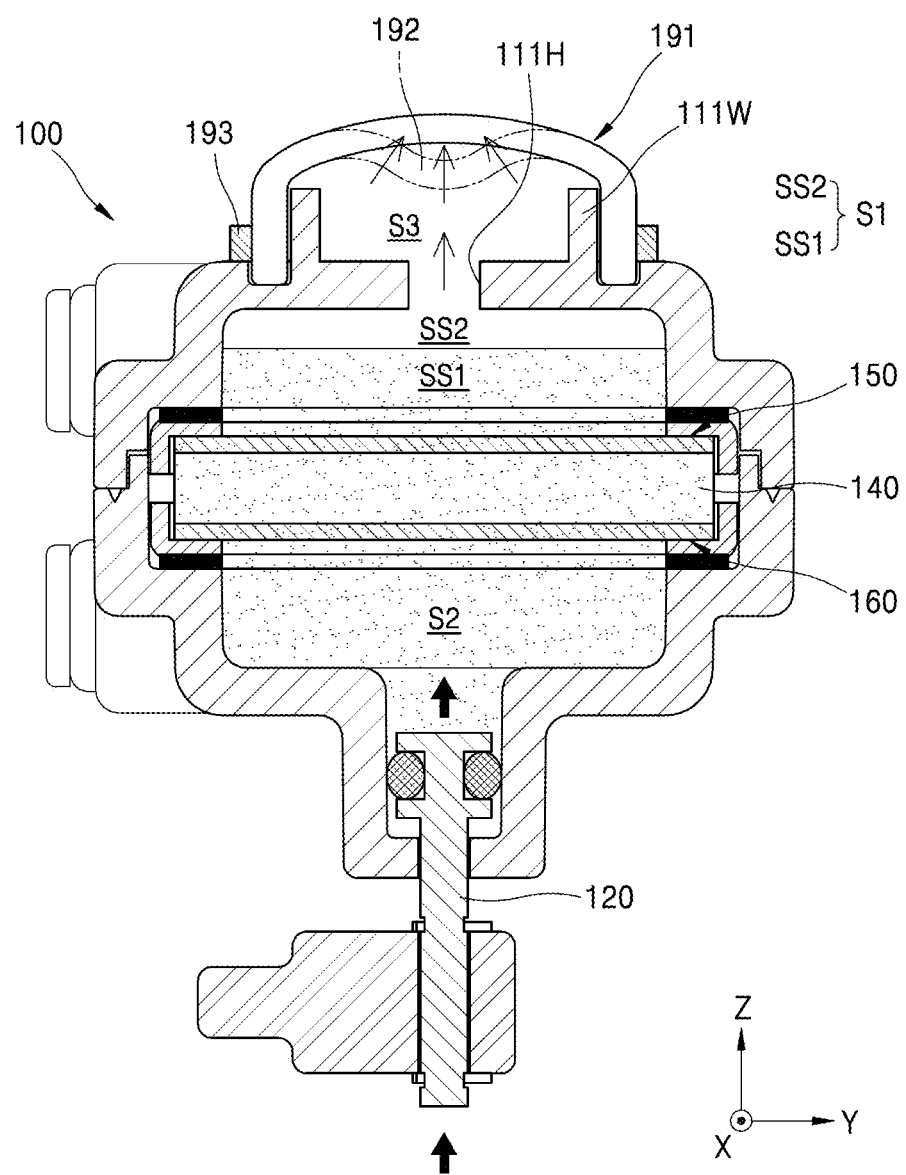

FIG. 7 is a perspective view of an electroosmotic pump according to another embodiment of the present disclosure. FIGS. 8A and 8B are cross-sectional views of the electroosmotic pump taken along line X-X' of FIG. 7. FIGS. 9A and 9B are schematic diagrams showing reactions of first and second electrode bodies around a membrane, according to embodiments of the present disclosure. FIGS. 10A to 10C are cross-sectional views for describing a reciprocating movement of a shaft.

Referring to FIGS. 5, and 7 to 10C, the pump 100 according to another embodiment of the present disclosure may include the housing 110, the shaft 120, the membrane 140, the first electrode body 150, the second electrode body 160, a deformation portion 191, and a first fluid.

FIGS. 4A to 10C are cross-sectional views for describing a reciprocating movement of a shaft. FIG. 4A shows a state before the shaft moves and FIGS. 10B and 10C show states after the shaft moves. FIG. 4A may be understood as a state before the voltage is applied to the first and second electrode bodies 150 and 160 by the power supply unit 200 as described above with reference to FIG. 9A.

Referring to FIG. 4A, the first fluid that is the liquid such as water exists in the internal space of the housing 110, and the volume of the first fluid in the internal space is less than the volume of the internal space. In the internal space, the region where the liquid does not exist, in more detail, the first space S1 of the housing 110 and a third space S3 that is an internal space of the deformation portion 191 include the second fluid including the gas such as air.

Referring to FIGS. 10A to 10C, the second fluid may exist in the first space S1, in particular, the third space S3 that is the internal space of the deformation portion 191, wherein the third space S3 communicates with the second sub-space SS2.

In the state of FIG. 10A, when the power supply unit 200 supplies the voltage to the first and second electrode bodies 150 and 160 as described above with reference to FIG. 9A, the reaction described above with reference to FIG. 9A occurs and the cations (e.g., hydrogen ions) move in the first direction (−Z direction in FIG. 10B) from the first space S1 to the second space S2.

Here, the first fluid (e.g., $H_2O$) in the first space S1 is moved with the cations in the first direction (−Z direction in FIG. 10B) through the membrane 140, and then, a pressure is generated. In addition, the shaft 120 linearly moves in the first direction due to the pressure as shown in FIG. 10B.

Referring to FIG. 10A, the deformation portion 191 according to another embodiment of the present disclosure communicates with a side of the housing 110 (upper side in FIG. 10A) in which the first space S1 is provided, and the first space S1 and the third space S3 that is the internal space of the deformation portion 191 may communicate with each other via the hole 111H formed in one surface (upper surface in FIG. 10A) of the housing 110, which faces the deformation portion 191.

Referring to FIG. 8A, the main body 111 may include the first sub-main body 111A and the second sub-main body 111B. The first and second sub-main bodies 111A and 111B may be coupled to each other with the membranes 140 therebetween.

The main body 111, in particular, the hole 111H is formed in the first sub-main body 111A, and the hole 111H is located opposite to the second sub-main body 111B that accommodates the shaft 120, with the membrane 140 in the center therebetween.

Referring to FIGS. 10A and 10B, an elastic portion 192 that may elastically deform may be formed in a side of the deformation portion 191 according to another embodiment of the present disclosure. The elastic portion 192 may be at a center portion of the deformation portion 191, and may be concave or convex with respect to an outer direction (upper direction in FIG. 10A) of the deformation portion 191.

Referring to FIGS. 10A to 10C, as the shape of the elastic portion 192 deforms, a volume of the third space S3 may increase or decrease.

The elastic portion 192 may deform according to an internal pressure of the internal space of the deformation portion 191, in particular, the internal pressure of the third space S3. Referring to FIG. 10A, a negative pressure may be generated in the third space S3.

The elastic portion 192 may have an elastic recovery force in a direction in which the elastic portion 192 is convex toward the outer direction (upper direction in FIG. 10A) of the deformation portion 191. As such, as shown in FIG. 10C, when the first fluid moves with the cations from the second space S2 to the first space S1, a space in which the second fluid such as the air is accommodated may be ensured as much as the third space S3, the force required for compressing the shaft 120 may be relatively reduced, and the compression may be easily performed.

When the first fluid (e.g., $H_2O$) in the first space S1 moves to the second space S2, a ratio of the volume of the first sub-space SS1 with respect to the volume of the first space S1 is reduced, whereas a ratio occupied by the second sub-space SS2 in the first space S1 increases.

On the contrary, referring to FIGS. 10B and 10C, when the power supply unit 200 changes the polarity of the voltage and supplies the voltage to the first and second electrode bodies 150 and 160 as described above with reference to FIG. 9B, the cations (e.g., hydrogen ions) and the first fluid (e.g., water) move in the second direction (Z-direction of FIG. 4) from the second space S2 to the first space S1, and the shaft 120 is moved to the original position as shown in FIG. 10A.

Referring to FIG. 10C, as the shaft 120 moves in the second direction (+Z direction in FIG. 10C), the first fluid moves with the cations in the second direction and the deformation portion 191, in particular, the elastic portion 192, may be deformed.

In detail, as the elastic portion 192 is deformed from a concave shape to a convex shape toward the outer direction of the deformation portion 191, the volume of the third space S3 increases and the shaft 120 may be easily moved and easily compressed.

In addition, when the first space S1 and the third space S3 are compressed, the deformation portion 191, in particular, the elastic portion 192, has the elastic recovery force in a direction of being convex, and thus, the compression may be more easily performed.

In addition, when a gas is generated as the reaction shown in FIGS. 9A and 9B occurs, the gas may be accommodated in the third space S3, and thus, a buffering function may be obtained.

As described above, referring to FIGS. 7, 8A, and 10A to 10C, the deformation portion 191 according to another embodiment of the present disclosure communicates with the housing 110 in which the first space S1 is provided and has the third space S3 provided therein, wherein the third space S3 is the internal space connecting to the first space S1 to be deformed. The deformation portion 191 may include a material such as silicon that may be elastically deformed.

In detail, the deformation portion 191 may be coupled to a side of the housing 110 (upper side in FIG. 8A), which faces the other side (lower side of FIG. 8A) of the housing 110, through which the shaft 120 reciprocates, based on the membrane 140.

The hole 111H is formed in one surface (upper surface in FIG. 8A) of the housing 110 facing the deformation portion 191, and the first space S1 and the third space S3 may communicate with each other. As such, as compared with an example in which the first space S1 is only provided, the force stored in the second fluid in the first space S1 may be removed, and thus, the forward and backward strokes of the shaft 120 may be accurately controlled.

Referring to FIGS. 10A to 10C, the elastic portion 192 that may elastically deform is formed in one side (upper side in FIG. 10A) of the deformation portion 191 according to another embodiment of the present disclosure, and the volume of the third space S3 may be changed as the elastic portion 192 is elastically deformed.

Referring to FIGS. 10A and 10B, a negative pressure is generated in the third space S3 before the reaction shown in FIG. 9A occurs, and the elastic portion 192 may be formed to be concave from the outer direction of the deformation portion 191.

When the reaction shown in FIG. 9B occurs as shown in FIG. 10C, the pressure increases due to the pressure of the first fluid, etc., and the elastic portion 192 has the elastic recovery force in a direction in which the elastic portion 192 is formed to be convex toward the outer direction of the deformation portion 191. Thus, the deformation portion 191 is deformed in a direction in which the volume of the third space S3 increases, and the force stored in the second fluid may be removed. Accordingly, the shaft 120 may be easily compressed and may be accurately controlled.

Referring to FIGS. 7, 8A, and 10A to 10C, a fixing member 193 according to another embodiment of the present disclosure is coupled to the housing 110 and the deformation portion 191, and makes the deformation portion 191 fixed on the housing 110.

In addition, the fixing member 193 may block leakage of the second fluid including the air from the third space S3, that is, the internal space of the deformation portion 191, to the outside.

The fixing member 195 is in close contact with an outer circumferential surface of the deformation portion 191 and may be installed on the housing 110.

Referring to FIGS. 7, 8A, and 10A to 10C, a sealing wall 111W protruding outward and being in close contact with an inner circumferential surface of the deformation portion 191 may protrude from one surface (upper surface in FIG. 8A) of the housing 110, which faces the deformation portion 191.

The inner circumferential surface of the deformation portion 191 is in close contact with the sealing wall 111W and the outer circumferential surface of the deformation portion 191 is in close contact with the fixing member 195 due to the sealing wall 111W, and thus, leakage of the fluid accommodated in the third space S3 to the outside may be prevented.

FIG. 8B is a cross-sectional view of the pump 100 according to another embodiment of the present disclosure. The pump shown in FIG. 8B has a similar structure as those of the pumps described above with reference to FIGS. 5, 7, 8A, and 9A, but may further include a breathable film 195 that covers the hole 111H formed in the housing 110 and is coupled to the housing 110 such that the first space S1 and the third space S3 may communicate with each other.

Referring to FIG. 8B, the hole 111H according to another embodiment of the present disclosure may be covered by the breathable film 195. Therefore, the second sub-space SS2 is not spatially connected to the outer space, that is, the third space S3 that is the internal space of the deformation portion 191, due to the breathable film 195.

The breathable film 195 is a film that blocks the liquid and transmits the gas, and thus the first fluid (e.g., water) of the pump 100 does not pass through the breathable film 190.

However, the second fluid in the pump 100 or the external air may pass through the breathable film 195, and in this case, the second fluid or the external air flows into the third space S3 that is the internal space of the deformation portion 191, and the force generated during the forward and backward movements of the shaft 120 may be prevented from being stored in the second fluid.

The pump 100 according to another embodiment of the present disclosure has the same structure, the same operating principles, and same effects as those of the pump 100 according to the embodiments of FIGS. 1 to 6 except for the structures of the deformation portion 191, the fixing member 193, and the third space S3, and thus, redundant descriptions are omitted.

Referring to FIGS. 8A and 8B, a diameter HD1 of the hole 111H in the pump 100 according to another embodiment of the present disclosure shown in FIG. 8A may be greater than a diameter HD2 of the hole 111H in the pump 100 of FIG. 8B, in which the breathable film 195 would not be provided.

As such, when the first fluid moves between the third space S3 and the first space S1 in FIG. 8A, generation of resistance against the movement of the first fluid due to the hole 111H may be reduced.

In addition, the diameter HD1 of the hole 111H in the pump 100 according to another embodiment of the present disclosure may be equal to a diameter of the sealing wall 111W, and then, the first fluid may sufficiently fluid between the third space S3 and the first space S1.

The diameter HD1 or HD2 of the hole 111H according to one or more embodiments may be variously set.

The pump 100 according to one or more embodiments of the present disclosure described above with reference to FIGS. 1 to 10C may be a small-sized pump used in a device for injecting drugs such as insulin. However, provided that the pump moves the shaft 120 linearly by using the above-described structure and mechanism, the use of the pump is not particularly restricted.

While the disclosure has been particularly shown and described with reference to exemplary embodiments thereof, it will be understood by those of ordinary skill in the art that various changes in form and details may be made therein without departing from the spirit and scope as defined by the following claims. Therefore, the scope sought to be protected of the disclosure shall be defined by the appended claims.

According to the present disclosure, an electroosmotic pump is provided. Also, one or more embodiments of the present disclosure may be applied to an insulin injection device that is industrially used for injecting insulin into a human body to be suitable for a change in the blood sugar of a patient.

What is claimed is:

1. An electroosmotic pump comprising:
a housing including a shaft hole;
a membrane disposed between a first space arranged in a direction away from the shaft hole and a second space adjacent to the shaft hole;
a first electrode body and a second electrode body arranged at opposite sides of the membrane;
a shaft extending to an outside of the housing through the shaft hole; and
a first fluid included in an internal space of the housing,
wherein the shaft is configured to reciprocate in a first direction from the first space to the second space and in a second direction opposite to the first direction.

2. The electroosmotic pump of claim 1, wherein a volume of the first fluid is less than a volume of the internal space.

3. The electroosmotic pump of claim 1, wherein the first fluid is provided in each of the first space and the second space, and a volume of the first fluid in the first space is less than a volume of the first space.

4. The electroosmotic pump of claim 3, wherein the first space includes a first sub-space occupied by the first fluid and a second sub-space, and a reciprocating movement of the shaft varies according to a ratio of a volume of the second sub-space to the volume of the first space.

5. The electroosmotic pump of claim 4, further comprising a second fluid occupying the second sub-space, wherein the first fluid is a liquid and the second fluid is a gas.

6. The electroosmotic pump of claim 5, wherein the housing includes a hole connected to the first space, and the hole is spatially separated from an outer space of the housing by a breathable film.

7. An electroosmotic pump comprising:
a housing including a shaft hole in a side thereof;
a shaft extending to an outside of the housing through the shaft hole;
a membrane arranged in an internal space that is defined by an inner surface of the housing and the shaft;
a first electrode body arranged at a first side of the membrane;
a second electrode body arranged at a second side of the membrane, wherein the second side is opposite to the first side; and
a fluid accommodated in the internal space, wherein the internal space includes a first space and a second space at opposite sides of the membrane, the fluid includes a first fluid in the first space, and a volume of the first fluid in the first space is less than a volume of the first space, and_wherein the shaft is configured to reciprocate in a first direction from the first space to the second space and in a second direction opposite to the first direction, and a reciprocation of the shaft is dependent on a flow of the fluid between the first space and the second space.

8. The electroosmotic pump of claim 7, wherein the first space is located far from the shaft such that the membrane is provided therebetween.

* * * * *